United States Patent
Haiat et al.

(10) Patent No.: US 12,082,985 B2
(45) Date of Patent: Sep. 10, 2024

(54) DEVICE AND METHOD FOR CONTROLLING THE STABILITY OF A DENTAL IMPLANT

(71) Applicants: Centre National de la Recherche Scientifique, Paris (FR); UNIVERSITE PARIS XII—VAL DE MARNE, Paris (FR); L'ASSISTANCE PUBLIQUE—HOPITAUX DE PARIS, Paris (FR)

(72) Inventors: Guillaume Haiat, Rungis (FR); Romain Vayron, Maisons-Alfort (FR)

(73) Assignees: CENTRE NATIONAL DE LA RECHERCHE SCIENTIFIQUE, Paris (FR); UNIVERSITE PARIS XII—VAL DE MARNE, Paris (FR); L'ASSISTANCE PUBLIQUE—HOPITAUX DE PARIS, Paris (FR)

( * ) Notice: Subject to any disclaimer, the term of this patent is extended or adjusted under 35 U.S.C. 154(b) by 939 days.

(21) Appl. No.: 17/048,018

(22) PCT Filed: Apr. 16, 2019

(86) PCT No.: PCT/EP2019/059739
§ 371 (c)(1),
(2) Date: Oct. 15, 2020

(87) PCT Pub. No.: WO2019/201888
PCT Pub. Date: Oct. 24, 2019

(65) Prior Publication Data
US 2021/0106415 A1     Apr. 15, 2021

(30) Foreign Application Priority Data
Apr. 16, 2018 (FR) .................................... 1853306

(51) Int. Cl.
*A61C 19/04* (2006.01)
*A61B 5/00* (2006.01)
(Continued)

(52) U.S. Cl.
CPC ............ *A61C 19/04* (2013.01); *A61B 5/4504* (2013.01); *A61B 5/4542* (2013.01);
(Continued)

(58) Field of Classification Search
CPC ..... A61C 19/04; A61C 8/0089; A61B 5/4504; A61B 5/4542; A61B 8/0858; A61B 8/0875; A61B 8/5223
See application file for complete search history.

(56) References Cited

U.S. PATENT DOCUMENTS 7,285,091 B2 * 10/2007 Blodgett .............. A61B 8/0875
                                                                          433/215
8,974,389 B2     3/2015 Pan et al.
(Continued)

FOREIGN PATENT DOCUMENTS

| CN | 102188291 A | 9/2011 |
| EP | 2503954 A1 | 10/2012 |
| WO | 2011064498 A1 | 6/2011 |

OTHER PUBLICATIONS

International Search Report issued in Application No. PCT/EP2019/059739, mailed on Jun. 26, 2019 (5 pages).
(Continued)

*Primary Examiner* — Ralph A Lewis
(74) *Attorney, Agent, or Firm* — HAUPTMAN HAM, LLP

(57) ABSTRACT

Device for inspecting the stability of a dental implant (1) in a bone (2), the implant having a free end (1*a*) and an end (1*b*) buried in the bone (2). The device comprises an ultrasonic transducer (12) for emitting and collecting an ultrasonic
(Continued)

wave reflected from a contact interface (4) between the implant (1) and the bone (2), and providing a measurement signal representing the reflected ultrasonic wave. The device also comprises a processing unit for computing, based on the measurement signal, an indicator (IN) whose value makes it possible to evaluate the integration of the implant (1) into the bone (2). The indicator (IN) corresponds to the average energy of the measurement signal over a time interval (t1-t2) starting at a first time (t1) and ending at a second time (t2). The first time (t1) is between 20 and 80 μs after the start of the emission of the ultrasonic wave.

16 Claims, 3 Drawing Sheets

(51) Int. Cl.
    *A61B 8/08*     (2006.01)
    *A61C 8/00*     (2006.01)

(52) U.S. Cl.
    CPC .......... *A61B 8/0858* (2013.01); *A61B 8/0875* (2013.01); *A61B 8/5223* (2013.01); *A61C 8/0089* (2013.01)

(56) References Cited

U.S. PATENT DOCUMENTS

| | | | |
|---|---|---|---|
| 10,390,919 B2* | 8/2019 | Pan | G01N 29/2418 |
| 11,678,842 B2* | 6/2023 | Lynch | A61B 5/4851 |
| | | | 623/16.11 |
| 2012/0244489 A1 | 9/2012 | Carnahan | |
| 2013/0122458 A1 | 5/2013 | Pan et al. | |

OTHER PUBLICATIONS

Written Opinion issued in International Application No. PCT/EP2019/059739, mailed on Jun. 26, 2019 (10 pages).

Vayron et al.; "Assessment of In Vitro Dental Implant Primary Stability Using an Ultrasonic Method;" World Federation for Ultrasound in Medicine and Biology; vol. 40, No. 12; Dec. 1, 2014; pp. 2885-2894; XP055530349 (10 pages).

Vayron et al.; "Comparison of Resonance Frequency Analysis and of Quantitative Ultrasound to Access Dental Implant Osseointegration;" Sensors; vol. 18, No. 5; May 2, 2018; XP055530340 (16 pages).

Examination Report issued in Indian Application No. 202047049205 mailed on Jul. 13, 2022 (6 pages).

H. Muhammed et al.; "Using Ultrasonic Spectrometry to Estimate the Stability of a Dental Implant Phantom;" Engineering; vol. 5, No. 10, pp. 570-574; Jan. 1, 2013; XP055530353 (5 pages).

* cited by examiner

DEVICE AND METHOD FOR CONTROLLING THE STABILITY OF A DENTAL IMPLANT

TECHNICAL FIELD

The present disclosure relates to a device and to a method for inspecting the stability of a dental implant inserted at least partially into a bone.

BACKGROUND

A dental implant is conventionally in the form of an artificial dental root, generally made of a titanium alloy, placed inside the bone of the upper or lower jaw. A dental prosthetic element is then screwed into the implant. After the dental implant has been fitted, a healing period is often necessary for the bone cells to colonize the buried surface of the implant and for said implant to be "osseointegrated", that is to say integrated into the bone, without the interposition of fibrous tissue at the bone-implant interface, or border, between the bone and the implant.

As the dental implant plays the role of intermediary between the prosthetic element and the jawbone and in particular transmits forces to the bone support, it has to be integrated properly therein. During the aforementioned healing period, the implant is left to rest in order to integrate into the bone, so that it is then able to withstand the loads that will be exerted thereon. After the healing period, the surgeon fits the prosthetic element in the dental implant. Measuring the proper integration of the implant into the bone, or osseointegration, is therefore essential for the success of the treatment, in particular in order to determine precisely when to end the healing period and load the implant with the prosthetic element.

Patent document EP 2503954 describes a device for inspecting the stability of a dental implant in a bone and an associated device. This method consists in computing, based on an echogram, an indicator whose value makes it possible to evaluate the osseointegration of the implant. Although this indicator is satisfactory under some conditions, there remains a need for an indicator that makes it possible to accurately evaluate the osseointegration of the implant under more general conditions.

GENERAL DISCLOSURE

The present disclosure relates to a device for inspecting the stability of a dental implant inserted at least partially into a bone, the implant having a free end emerging from the surface of the bone and an end buried in the bone, located opposite the free end. This device comprises an ultrasonic transducer adapted to:
  be coupled directly or indirectly to the implant,
  emit an ultrasonic wave propagating inside the implant toward the buried end,
  collect the ultrasonic wave reflected from a contact interface between the implant and the bone, and provide a measurement signal representing the reflected ultrasonic wave.

The device also comprises a processing unit adapted to compute, based on the measurement signal, an indicator whose value makes it possible to evaluate the integration of the implant into the bone.

The proposed indicator corresponds to the average energy of the measurement signal, over a time interval t1-t2 starting at a first time t1 and ending at a second time t2, the first time t1 being between 20 and 80 µs after the start of the emission of the ultrasonic wave by the transducer. Such an indicator proves to be particularly sensitive to the osseointegration of the implant and therefore makes it possible to evaluate it accurately.

The present disclosure also relates to a method for inspecting the stability of a dental implant inserted at least partially into a bone, the implant having a free end emerging from the surface of the bone and an end buried in the bone, located opposite the free end. The method comprises the following steps:
  emitting an ultrasonic wave propagating inside the implant toward the buried end, collecting the ultrasonic wave reflected from a contact interface between the implant and the bone, and providing a measurement signal representing the reflected ultrasonic wave,
  computing said indicator based on the measurement signal.

Of course, the abovementioned device may be used to implement the method.

In addition to the abovementioned features, the proposed device and method may have one or more of the following features, considered on their own or in technically feasible combinations.

The first time t1 is between 30 and 60 µs. This makes it possible to further improve the sensitivity of the indicator.

The second time t2 is separated from the first time t1 by at least 5 µs (that is to say t2≥t1+5 µs) and at most equal to 200 µs.

The ultrasonic transducer is adapted to emit an ultrasonic wave whose center frequency is at least equal to 5 MHz. Below this value, the measurement signal that is collected is less representative of the bone-implant interface, and the computed indicator therefore does not characterize this interface as well. In particular, the center frequency may be at least equal to 8 MHz, and for example approximately equal to 10 MHz. Ultrasonic transducers having a center frequency of 10 MHz are readily available on the market at low cost, and this frequency is well-suited to the intended application.

The ultrasonic transducer has an active surface adapted to be in contact with the free end of the implant, directly or via an intermediate component, parallel to a bearing surface defined by the free end of the implant, so as to emit an ultrasonic wave propagating inside the implant in a direction of propagation perpendicular to the active surface of the transducer.

The processing unit comprises amplification means for amplifying the measurement signal, before computing the indicator, the measurement signal being amplified with a gain that is adjusted so as to achieve saturation of the signal up to the first time, but not beyond this. Moreover, the gain may be variable as a function of time and increase, for example continuously or in successive increments, between the first and second times. This makes it possible to increase the size of the time interval t1-t2 without achieving saturation of the signal, and therefore to achieve a gain in terms of sensitivity.

The abovementioned features and advantages, as well as others, will become apparent on reading the following detailed description of exemplary embodiments of the proposed device. This detailed description refers to the accompanying drawings.

BRIEF DESCRIPTION OF THE DRAWINGS

The accompanying drawings are schematic and are not to scale; they are intended primarily to illustrate the principles of the invention.

FIG. 4 is a photograph of four identical dental implants 1, inserted into a block of resin with different levels of pressing-in.

DETAILED DESCRIPTION OF EXAMPLE(S)

A few exemplary embodiments are described in detail below, with reference to the accompanying drawings. These examples illustrate the features and the advantages of the invention. It is however recalled that the invention is not limited to these examples.

Figure 1:
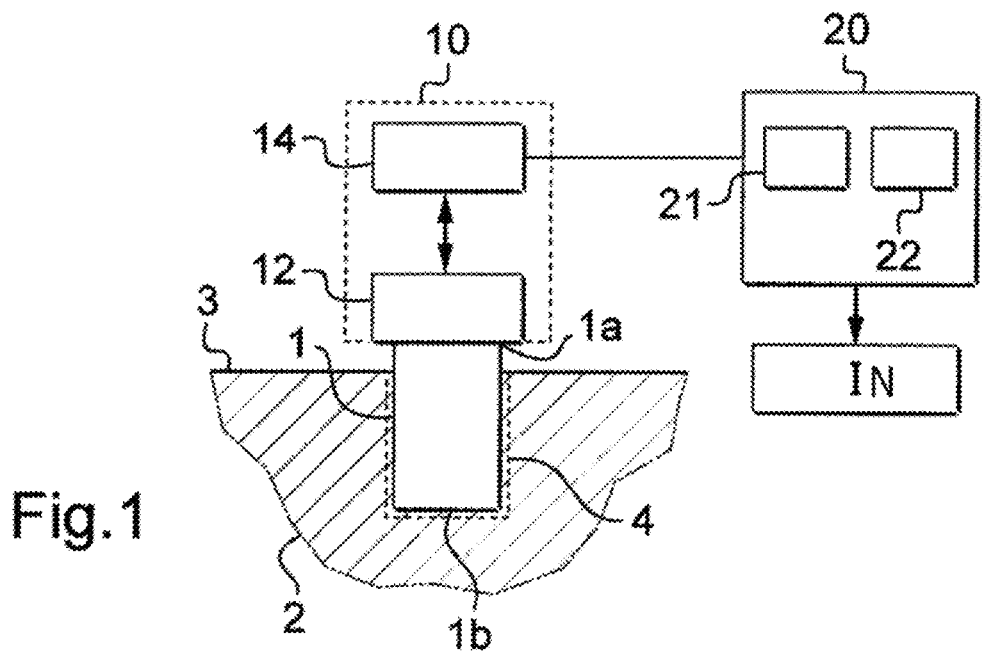
FIG. 1 is an overall schematic depiction of one example of an inspection device.

FIG. 1 shows one example of a device for inspecting the stability of a dental implant inserted into a bone 2. The dental implant 1 is shown schematically in the form of a cylinder. In reality, however, such an implant 1 has a tapered shape and an external thread, so as to be able to be screwed into the bone 2. For example, the implant has an average diameter of 2.5 to 5.5 mm in diameter and a length of 6 to 16 mm. The dental implant is typically made of a titanium alloy. Once it is anchored in the bone 2, the implant 1 has a free end 1a emerging from the surface 3 of the bone 2, opposite an end 1b buried in the bone 2, such that the free end 1a of the implant 1 is accessible in vivo.

The inspection device primarily comprises an ultrasonic sensor 10 and a computing unit 20. The ultrasonic sensor 10, which is piezoelectric, comprises an ultrasonic transducer 12 for emitting an ultrasonic wave in pulsed mode and receiving the echoes resulting from the reflection of the ultrasonic wave propagating in the implant, and a control circuit 14 for controlling the ultrasonic transducer 12. The ultrasonic transducer 12 is intended to be used in ultrasound mode and is placed such that its active surface is coupled, directly or indirectly (that is to say by means of an intermediate component, not shown), to the free end 1a of the implant, and such that this active surface is substantially parallel to the circular bearing surface defined by the free end 1a of the implant. The free end of the implant 1 is thus used as a reception site for positioning the transducer 12 or the intermediate component.

When an intermediate component (not shown) is used to couple the transducer 12 to the implant 1, it is adapted to transmit the ultrasonic wave between the transducer 12 and the implant 1. In order to allow this transmission, the intermediate component may be fastened mechanically, on one side, to the active surface of the transducer 12 and, on the other side, to the implant 1. It is fastened to the active surface of the transducer 12 for example by adhesive bonding, screwing or crimping. It is fastened to the implant 1 for example by screwing inside a cavity formed in the implant 1. Such a cavity (not shown) opens at the free end 1a of the implant and may extend to a greater or lesser depth within the implant 1 in the direction of its buried end 1b.

Under these conditions, the ultrasonic wave emitted by the transducer 12 may propagate inside the implant 1, perpendicular to the active surface of the transducer 12, from the free end 1a of the implant toward its buried end 1b, while at the same time promoting the phenomenon of interaction of the ultrasonic wave, which propagates in the implant, with a bone-implant contact interface 4 located at the border between the outer surface of the implant and the bone 2 surrounding it. This interaction phenomenon is essential, as will become apparent hereinafter.

The control circuit 14 comprises an electrical pulse generator that is used to excite the piezoelectric element of the transducer 12, which converts the received electrical pulses into a corresponding ultrasonic wave, which then propagates in the implant 1 toward the buried end 1b. The electrical pulse generator produces for example short-pulse signals or square-wave signals with rapid rising and falling edges. The control circuit 14 also comprises a reception circuit receiving the electrical signal, or measurement signal, delivered by the ultrasonic transducer 12 and corresponding to the ultrasonic wave reflected from the contact interface 4 and received by the transducer 12. The computing unit 20, connected to the sensor 10, for example by way of a coaxial transmission line, primarily comprises a computer memory 21 for storing the electrical signal representative of the reflected ultrasonic wave, collected by the reception circuit of the control circuit, and a processing unit 22 configured so as to process the stored signal, as described hereinafter. This computing unit 20 may be an independent unit such as a microcontroller or a personal computer. Various equipment may be added, such as display means and a printing means.

Figure 2:
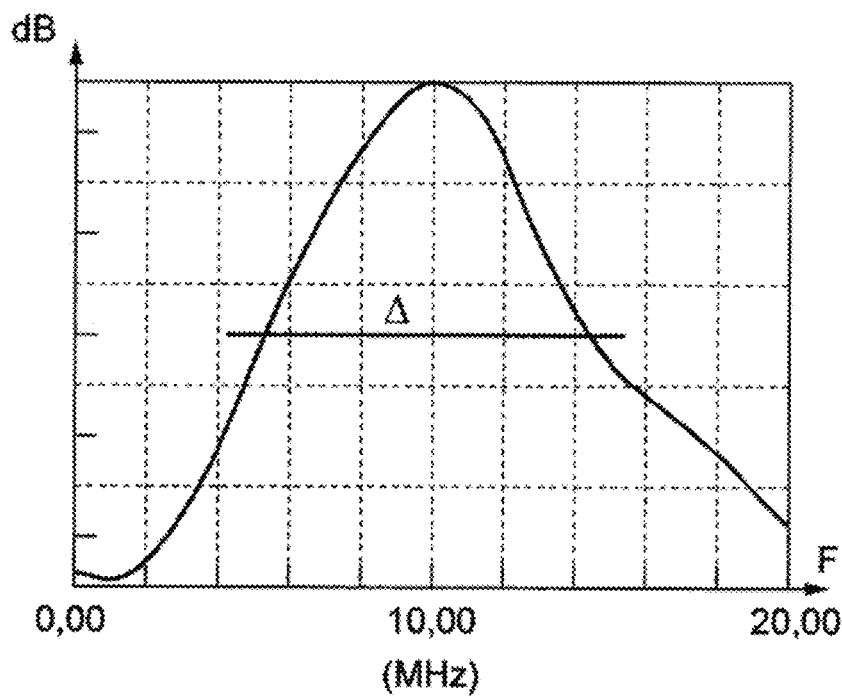
FIG. 2 shows the emission spectrum of the signal corresponding to the ultrasonic wave that is used.

Given the intended application, the center frequency of the emitted ultrasonic wave is preferably chosen to be at least equal to 5 MHz, in particular at least equal to 8 MHz. The bandwidth measured at −6 dB may be of the order of 80% of the center frequency. The lower limit of the bandwidth may be greater than or equal to 30 MHz. FIG. 2 shows an emission spectrum of the signal corresponding to an ultrasonic wave emitted with a center frequency equal to 10 MHz and a bandwidth A of between 6 and 14 MHz.

Figure 3:
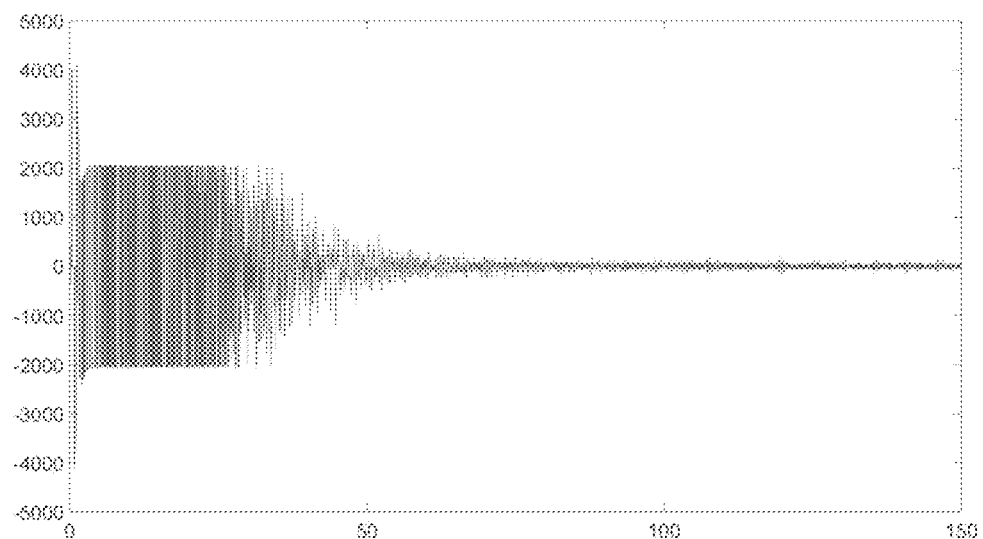
FIG. 3 is one example of a measurement signal obtained by way of the device of FIG. 1.

The pulse width of the electrical signal sent to the transducer 12 by the control circuit 14 is preferably chosen to be less than or equal to half a period corresponding to the resonant frequency of the ultrasonic transducer 12. For example, for a center frequency equal to 10 MHz, the pulse width is 50 ns. One example of a measurement signal, or echogram, obtained when inspecting the stability of an implant is shown in FIG. 3. The amplitude of the signal, on the ordinate, is given in arbitrary units. The time, on the abscissa, is given in µs (that is to say $10^{-6}$ s). In this example, the signal has been amplified with a gain of 70 dB, so as to achieve saturation of the signal up to t1=40 µs, the signal no longer being saturated thereafter.

The processing of the measurement signal representing the reflected ultrasonic wave may comprise several steps, but essentially consists in computing an indicator IN whose value makes it possible to evaluate the integration of the implant into the bone.

This indicator IN corresponds to the average energy of the measurement signal, over a time interval t1-t2 starting at a time t1 and ending at a time t2.

The average energy may be determined by computing the integral of the absolute value of the amplitude of the signal squared, over the time interval t1-t2. In this case, it is possible to have:

$$IN = \int_{t_1}^{t_2} |M(t)|^2 dt$$

where M(t) denotes the measurement signal.

The average energy may however be determined differently, without departing from the scope of the invention. For example, the indicator IN may be computed using the following formula:

$$IN = \int_{t_1}^{t_2} |M(t)| dt$$

Instead of considering the square of the amplitude of the signal, or the absolute value of the amplitude of the signal, it is also possible to consider the envelope E(t) of the measurement signal or any other physical variable linked to the energy contained in the signal, in the time window under consideration.

In their research that led to the invention, the inventors discovered that there was an optimal value for the choice of the time t1 for optimizing the sensitivity of the indicator and, thus, for more accurately evaluating the osseointegration of the implant. Surprisingly, relatively high values should be chosen for t1. This discovery is illustrated by the following series of experiments.

(Hardware and Method)

Figure 4:
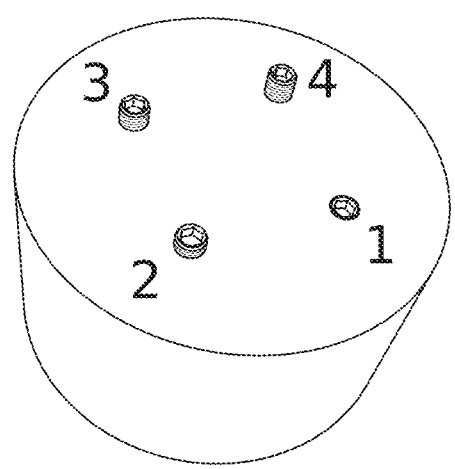

The experiments were carried out using an ultrasonic probe of the type in FIG. 1 but equipped with an intermediate component between the transducer 12 and the implant 1. Four strictly identical dental implants 1 were inserted into a block of resin with different levels of pressing-in, as shown in the photograph of FIG. 4.

The implants are numbered in order of decreasing pressing-in. As the implants are pressed in to a greater or lesser extent, they are more or less stable. Thus, implant number 1, pressed completely into the resin, is highly stable. Its stability corresponds to that of a perfectly osseointegrated implant. By contrast, implant number 4, hardly pressed into the resin at all, is highly unstable. Its stability corresponds to that of an implant that is not at all or only very slightly osseointegrated.

Implants numbers 2 and 3 correspond, respectively, to a relatively stable and relatively unstable implant. The results that were obtained with implants numbers 2 and 3 were compared in order to evaluate the sensitivity of the indicator IN.

The indicator IN is computed in a time window between t1 and t2, it being understood that the second time t2 is after the first time t1, that is to say t2>t1. Generally speaking, the value of t2 is chosen so as to achieve an acceptable compromise between a sufficient duration to obtain relevant information and the need for a satisfactory signal-to-noise ratio. With these general conditions being met, the inventors observed that the value of t2 did not significantly influence the sensitivity of the indicator IN as long as the duration of the window t1-t2 was at least equal to approximately 5 μs. Therefore, in the experiments that were carried out, the value of t2 was chosen to be equal to 150 μs for all of the measurements. The value of t2 may however more generally be chosen between t1+5 μs and 200 μs. For example, for t1=40 μs, t2 may be chosen between 45 and 200 μs.

A variation in the value of t1 between 5 and 100 μs was considered. For each value of t1 considered, the same procedure was used to adjust the gain so as to be able to view the signal with a conventional digitizer. This procedure consists in adjusting the gain so as to achieve saturation of the signal up to the start of the time window under consideration (therefore around the time t1), the signal no longer being saturated thereafter. This is illustrated in FIG. 3, which shows one example of a measurement signal obtained when inspecting the stability of implant number 3. The value of t1 under consideration is 40 μs. The signal was amplified and the gain adjusted to 70 dB, so as to achieve signal saturation up to 40 μs, the signal no longer being saturated thereafter.

Figure 5:
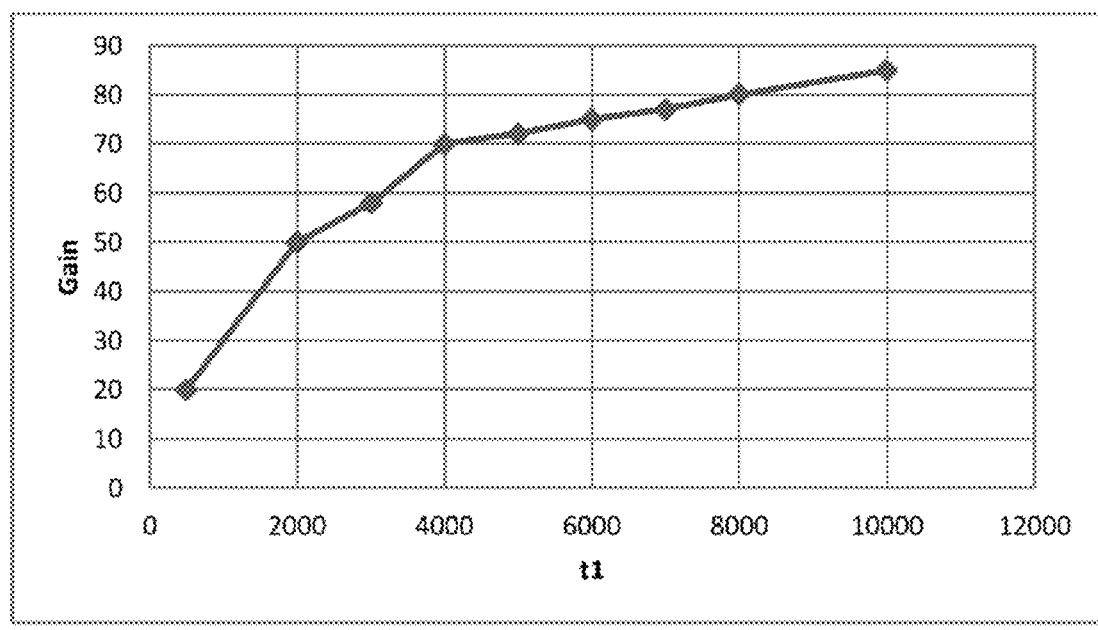
FIG. 5 is a graph showing the variation in the gain applied to the measurement signal, expressed in dB, as a function of t1, expressed in hundredths of µs (that is to say $10^{-8}$ s).

This procedure was applied considering implant number 3, since this is the implant that makes it possible to achieve a maximum value of the signal. It should be noted that it is not necessary to have very precise adjustment of the gain, but that it should be the same for the two implants (numbers 2 and 3) under consideration and for the same value of t1. FIG. 5 shows the variation in the gain, expressed in dB, as a function of t1, expressed in hundredths of μs (that is to say $10^{-8}$ s). The gain increases as a function of t1 because the more the signal is measured at a high time, the more it is necessary to amplify the signal, in the knowledge that said signal decreases as a function of time.

Once the value of the gain was determined for each value of t1, three measurements were taken with each implant and each value of t1, using the gain determined beforehand. The results obtained with implants numbers 2 and 3 were compared and a sensitivity S(t1) of the indicator IN was estimated for each value of t1. When the values of the indicator IN do not exhibit any significant differences between the two implants, the sensitivity S was set equal to 0. Otherwise, the sensitivity S is given by the relative variation in the average of the indicators obtained for implants 2 and 3, that is to say:

$$S(t1) = \frac{(M(t1, 3) - M(t1, 2)) * 200}{M(t1, 3) + M(t1, 2)},$$

where M(t1,i) corresponds to the average of the indicators obtained for implant number i and the indicator computed with t1. The value of S therefore increases with the sensitivity of the indicator IN.

(Results and Conclusion)

Figure 6:
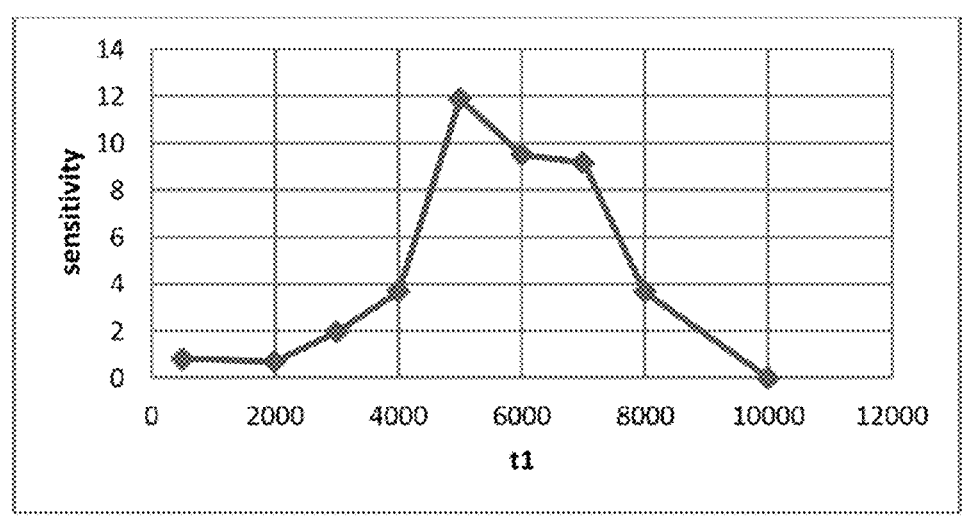
FIG. 6 is a graph showing the variation in the sensitivity S, expressed as a percentage, as a function of t1, expressed in hundredths of µs (that is to say $10^{-8}$ s).

FIG. 6 shows the variation in the sensitivity S, without any unit, as a function of t1, expressed in hundredths of μs (that is to say $10^{-8}$ s). Surprisingly, an optimal value is achieved for a value of t1 situated around 50 μs. The sensitivity is good, that is to say greater than or close to 4, for values of t1 between 40 and 80 μs.

At present, it is difficult to explain the existence of an optimal value for t1 and why this value is relatively high. The following hypothesis may however be put forth.

Considering a relatively lengthy propagation time, the ultrasonic wave makes a large number of round trips in the implant (which behaves like a waveguide). Therefore, the greater the time, the more the amplitude of the measurement signal is sensitive to variations in the conditions at the boundaries of the implant, because the ultrasonic wave will have made more round trips in the implant, and therefore interacts more significantly with the bone-implant interface. Therefore, if the value of t1 is too low, the useful signal for computing the indicator IN is within relatively short times due to the exponential decrease in the signal, thereby making it impossible to achieve good sensitivity due to the nature of the interaction between the ultrasonic wave and the implant. On the other hand, if the value of t1 is too high, the signal becomes highly affected by noise, and it is not possible to achieve good sensitivity either.

Finally, it will be noted that the experiments carried out with a dental implant inserted (at least partially) into a bone are consistent with the abovementioned results achieved for an implant inserted into a resin. In particular, these experiments also demonstrate the existence of an optimal value for t1 and that this optimal value is relatively high. However, although it is relatively high, the optimal value of t1 is generally lower than the optimal value obtained with the resin.

The invention claimed is:

1. A device for inspecting the stability of a dental implant inserted at least partially into a bone, the implant having a free end emerging from the surface of the bone and an end buried in the bone, located opposite the free end, the device comprising:
   an ultrasonic transducer adapted to be coupled directly or indirectly to the implant, emit an ultrasonic wave propagating inside the implant toward the buried end, collect the ultrasonic wave reflected from a contact interface between the implant and the bone, and provide a measurement signal representing the reflected ultrasonic wave,
   a processing unit adapted to compute, based on the measurement signal, an indicator whose value makes it possible to evaluate the integration of the implant into the bone,
   characterized in that the indicator corresponds to the average energy of the measurement signal over a time interval starting at a first time and ending at a second time, and in that the first time is between 40 and 80 µs after the start of the emission of the ultrasonic wave by the transducer.

2. The device as claimed in claim 1, wherein the first time is between 40 and 60 µs.

3. The device as claimed in claim 1, wherein the second time is separated from the first time by at least 5 µs and at most equal to 200 µs.

4. The device as claimed in claim 1, wherein the ultrasonic transducer is adapted to emit an ultrasonic wave whose center frequency is at least equal to 5 MHz, in particular at least equal to 8 MHz.

5. The device as claimed in claim 1, wherein the ultrasonic transducer has an active surface adapted to be in contact with the free end of the implant, directly or via an intermediate component, parallel to a bearing surface defined by the free end of the implant, so as to emit an ultrasonic wave propagating inside the implant in a direction of propagation perpendicular to the active surface of the transducer.

6. The device as claimed in claim 1, wherein the processing unit comprises amplification means for amplifying the measurement signal before computing the indicator, the measurement signal being amplified with a gain that is adjusted so as to achieve saturation of the signal up to the first time, but not beyond this.

7. The device as claimed in claim 1, wherein the processing unit comprises amplification means for amplifying the measurement signal before computing the indicator, the measurement signal being amplified with a gain that is variable as a function of time and increases between the first and second times.

8. A method for inspecting the stability of a dental implant inserted at least partially into a bone, the implant having a free end emerging from the surface of the bone and an end buried in the bone, located opposite the free end, the method comprising the following steps:
   emitting an ultrasonic wave propagating inside the implant toward the buried end, collecting the ultrasonic wave reflected from a contact interface between the implant and the bone, and providing a measurement signal representing the reflected ultrasonic wave,
   computing, based on the measurement signal, an indicator whose value makes it possible to evaluate the integration of the implant into the bone,
   characterized in that the indicator corresponds to the average energy of the measurement signal over a time interval starting at a first time and ending at a second time, and in that the first time is between 40 and 80 µs after the start of the emission of the ultrasonic wave by the transducer.

9. The method as claimed in 8, wherein the emitted ultrasonic wave has a center frequency at least equal to 8 MHz.

10. The method as claimed in claim 8, wherein the first time is between 40 and 60 µs.

11. The method as claimed in claim 8, wherein the second time is separated from the first time by at least 5 µs and at most equal to 200 µs.

12. The method as claimed in claim 8, wherein the emitted ultrasonic wave has a center frequency at least equal to 5 MHz, in particular at least equal to 8 MHz.

13. The method as claimed in claim 8, wherein, before computing the indicator, the measurement signal is amplified with a gain that is adjusted so as to achieve saturation of the signal up to the first time, but not beyond this.

14. The method as claimed in claim 8, wherein the gain is variable as a function of time and increases between the first and second times.

15. The device as claimed in claim 1, wherein the first time is 50 µs.

16. The device as claimed in claim 1, wherein the ultrasonic transducer is adapted to emit an ultrasonic wave whose center frequency is at least equal to 8 MHz.

* * * * *